(12) United States Patent
Brueggerhoff et al.

(10) Patent No.: US 8,560,510 B2
(45) Date of Patent: Oct. 15, 2013

(54) COMPUTER SYSTEM AND METHOD FOR CREATING AT LEAST ONE MACHINE-READABLE FILE FOR A MEDICAL TREATMENT APPARATUS

(75) Inventors: Arnd Brueggerhoff, Schwerin (DE); Martin Gruendken, Rosbach (DE); Andreas Ripken, Neu-Anspach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 13/265,388

(22) PCT Filed: Apr. 22, 2010

(86) PCT No.: PCT/EP2010/002492
§ 371 (c)(1),
(2), (4) Date: Nov. 29, 2011

(87) PCT Pub. No.: WO2010/121820
PCT Pub. Date: Oct. 28, 2010

(65) Prior Publication Data
US 2012/0102010 A1    Apr. 26, 2012

(30) Foreign Application Priority Data

Apr. 24, 2009  (DE) .................. 10 2009 018 806

(51) Int. Cl.
*G06F 17/30*  (2006.01)
(52) U.S. Cl.
USPC .............. 707/702; 707/705; 705/2; 705/7.27; 715/744; 702/185; 700/30
(58) Field of Classification Search
USPC .............. 707/705, 702; 705/2, 7.27; 715/744; 702/185; 700/30
See application file for complete search history.

(56) References Cited

U.S. PATENT DOCUMENTS

| | | | |
|---|---|---|---|
| 5,230,061 A | 7/1993 | Welch | |
| 7,850,069 B2 * | 12/2010 | Taniguchi et al. | 235/375 |
| 8,090,595 B2 * | 1/2012 | Hartman | 705/3 |
| 2002/0101451 A1 | 8/2002 | Duemler | |
| 2004/0111294 A1 * | 6/2004 | McNally et al. | 705/2 |
| 2007/0215545 A1 | 9/2007 | Bissler et al. | |
| 2010/0065624 A1 * | 3/2010 | Taniguchi et al. | 235/376 |
| 2010/0153167 A1 * | 6/2010 | Kretzschmar et al. | 705/9 |
| 2010/0231944 A1 * | 9/2010 | Takahashi | 358/1.13 |
| 2011/0131058 A1 * | 6/2011 | McNally et al. | 705/2 |

FOREIGN PATENT DOCUMENTS

EP    0 608 762 A1    8/1994

OTHER PUBLICATIONS

International Search Report for PCT/EP2010/002492, mailed on Jun. 25, 2010.

* cited by examiner

*Primary Examiner* — Dennis Truong
(74) *Attorney, Agent, or Firm* — Kenyon & Kenyon LLP

(57) ABSTRACT

The invention proposes a computer system for creating at least one machine-readable file for a medical treatment apparatus, with a database for providing at least one parameter set, an input device for inputting data regarding the flow behavior of the medical treatment apparatus as parameter set; an output device for creating and outputting a flow definition output file taking into account the input data; and a converting device for creating at least one machine-readable file or machine-readable data in a storage medium utilizing at least the parameter set. Further, a corresponding method, a data medium and a medical apparatus are specified.

20 Claims, 12 Drawing Sheets

| | A | B | C | D | E | F | G | H | I | J | K | L | M | N | O | P | Q | R | S | T |
|---|---|---|---|---|---|---|---|---|---|---|---|---|---|---|---|---|---|---|---|---|
| 1 | Alarm parameter spreadsheet, version 1.0.0 | | | | | | | | | | | | | | | | | | | |
| 2 | CPU | | | | | | | | | | | | | | | | | | | |
| 3 | [...] | | | | | Variable | Data type raw data | Preprocessing type | Parameter_1 | Scaling_P1 | Parameter_2 | Scaling_P2 | Parameter_3 | Scaling_P3 | Parameter_4 | Scaling_P4 | Variable | Data type preprocessing value | Comment | |
| | | | | | | Raw data | | | | | Preprocessing parameters | | | | | | Preprocessing value | | | |
| 4 | CPU n | | | | | | enum | enum | long | long | long | long | long | long | long | long | | enum | | |
| 5 | | | | | | Pressure_PS_01_CalcValue | si | AVGA | 6 | | | | | | | | Pressure_PS_01_CalcValue_AVGA_6 | si | | EOL |
| 6 | CPU 2 | | | | | Pressure_PS_02_CalcValue | si | AVGA | 6 | | | | | | | | Pressure_PS_02_CalcValue_AVGA_6 | si | | EOL |
| 7 | CPU 1 | | | | | | | | | | | | | | | | | | | EOL |

Fig. 4

| | | | | | | Enable | Preprocessing value | Parameters for detection status | | | |
|---|---|---|---|---|---|---|---|---|---|---|---|
| | A | B | C | D | E | F | G | H | I | J | K |
| 1 | Alarm parameter spreadsheet, version 1.0.0 | | | | | | | | | | |
| 2 | | | | | CPU | | | | | | |
| 3 | | | | | [*] | Variable | Variable | Data type preprocessing value | Detection function | Limit value (literal) | Limit value (DBVar) |
| 4 | | | | | CPU 1 | | | enum | enum | long | Variable |
| | | | | | CPU 2 | | | | | | |
| | | | | | ... | | | | | | |
| | | | | | CPU n | | | | | | |
| 8 | | 1 | 1 | | | T0_Part_UserLowerThresholdInactive_Counter_EQ0 | Pressure_PS_01_CalcValue_AVGA_6 | si | LT | | CPU1_USER_Pressure_Art_LowerWindowLimit |
| 9 | | 1 | 1 | | | T0_Part_UserUpperThresholdInactive_Counter_EQ0 | Pressure_PS_01_CalcValue_AVGA_6 | si | GT | | CPU1_USER_Pressure_Art_UpperWindowLimit |
| 10 | | 1 | 1 | | | 1 | Pressure_PS_01_CalcValue_AVGA_6 | si | LT | | T0_Part_ExtendedLowerScalesLimit |
| 11 | | 1 | 1 | | | 1 | Pressure_PS_01_CalcValue_AVGA_6 | si | GT | | T0_Part_ExtendedUpperScalesLimit |
| 12 | | | | | | | | | | | |
| 13 | | 1 | 1 | | | 1 | CPU3_Status_DME_01_open_active | uc | EQ | 1 | |
| 14 | | 1 | 1 | | | CPU3_Status_DME_01_open_active_EQ1 | Pressure_PS_01_CalcValue_AVGA_6 | si | GT | 120 | |
| 15 | | | | | | | | | | | |

Fig. 5a

| L | M | N | O | P |
|---|---|---|---|---|
| enum | [""] | Variable | | |
| Data type limit value | EZ-Prefix | Detection status | Comment | |
| si | | T0_Part_UserLowerThresholdInactive_Counter_EQ0_Pressure_PS_01_CalcValue_AVGA_6_LT_CPU1_USER_Pressure_Art_LowerWindowLimit | Lower limit active after delay, and value smaller than limit value | EOL |
| si | | T0_Part_UserUpperThresholdInactive_Counter_EQ0_Pressure_PS_01_CalcValue_AVGA_6_LT_CPU1_USER_Pressure_Art_UpperWindowLimit | Upper limit active after delay, and value bigger than limit value | EOL |
| si | | Pressure_PS_01_CalcValue_AVGA_6_LT_T0_Part_ExtendedLowerScalesLimit | Value smaller than absolute lower limit value | EOL |
| si | | Pressure_PS_01_CalcValue_AVGA_6_LT_T0_Part_ExtendedUpperScalesLimit | Value bigger than absolute upper limit value | EOL |
| uc | | CPU3_Status_DME_01_open_active_EQ1 | Pressure measure unit 1 has to be opened | EOL |
| si | | CPU3_Status_DME_01_open_active_EQ1_Pressure_PS_01_CalcValue_AVGA_6_GT120 | Pressure measure unit 1 has to be opened, but pressure above 120mmHg | EOL |

Fig. 5b

| A | B | C | D | E | F | G |
|---|---|---|---|---|---|---|
| 1 Alarm parameter spreadsheet, version 1.0.0 ||||||||
| 2 | CPU ||||| Parameters for detection status ||
| 3 ||| [" "] || Variable | Detection status | Comment |
| 4 | CPU 1 ||||||
|   | CPU 2 ||||||
|   | ... ||||||
|   | ... ||||||
|   | CPU n ||||||
| 5 ||||||||
| 6 | 1 |||| T0_Part_UserLowerThresholdInactive_Counter_EQ0_Pressure_PS_01_CalcValue_AVGA_6_LT_CPU1_USER_Pressure_Art_LowerWindowLimit | Lower limit active after delay, and value smaller than limit value |
| 7 ||||||||

| | | | | | |
|---|---|---|---|---|---|
| relevant for process/es | [" "] | HD-process | 1 | | |
| | | HDF-process | 1 | | |
| | | process 3 | 1 | | |
| | | ... | 1 | | |
| | | ... | 1 | | |
| | | process X | 1 | | |
| relevant for sub-process/es | [x\|0] | anticoagulation heparin | x | | |
| | | sub-process 2 | x | | |
| | | ... | x | | |
| | | sub-process Y | x | | |
| relevant for system status | [" "] | device test | | | |
| | | set up | | | |
| | | fill | | | |
| | | rinse | | | |
| | | ... | | | |
| | | ... | | | |
| | | treatment | 1 | | |
| | | ... | ☐ | | |
| | | ... | | | |
| | | switch off | | | |
| not relevant for process status | [" "] | SZ_blood | 1 | | |
| | | SZ_heparin | | | |
| | | ... | | | |
| | | ... | | | |
| | | SZ_PathDiscconn | | | |
| not relevant after process status for time | unsigned int [s] | SZ_blood | | | |
| | | SZ_heparin | | | |
| | | ... | | | |
| | | ... | | | |
| | | SZ_PathDiscconn | | | |
| AWI parameter | ui | priority | 31 | | |
| | ui | Group | 220 | | |
| | [" "] | Change in system status allowed | | | |

| AP | AQ | AR | AS | AT | AU | AV | AW | AX | AY | AZ |
|---|---|---|---|---|---|---|---|---|---|---|
| eSTRING_ID | ui | eGLOBAL_OBJECTS | | | Variable | | | eSTRING_ID | eBITMAP_ID | eFRAME_COLOR |
| AWI-Text-ID | AWI-Text-Index | Embedded Alarm Object | Text Parameter 1 | Text Parameter 2 | Text Parameter 3 | Text Parameter 4 | Text Parameter 5 | Help text ID | Auxiliary picture | Frame color |
| | | | | | Message parameters, part 1 | | | | | |
| S_AWI_TEXT_5678 | 5678 | ACHTUNG.BMP | PS_01_CalcValue_AVGA_6 | | | | | S_AWI_HELP_5678 | PS01.BMP | MSG_FRAME_RED |

Fig. 6c

| BA | BB | BC |
|---|---|---|
| Message parameters, part 2 | | |
| eACOUSTIC_ALARM | eOPTICAL_ALARM | eNURSE_CALL |
| Acoustic signal | Optical signal | Nurse call |
| MSG_ACOUSTIC_ALARM | MSG_OPTICAL_RED | MSG_NURSECALL_ON |

Fig. 6d

| BD | BE | BF | BG | BH | BI | BJ | BK | BL | BM | BN |
|---|---|---|---|---|---|---|---|---|---|---|
| eOPTION_POS | eAWI_RESPONSE | eSTRING_ID | ui | eAWI_RESPONSE | eSTRING_ID | ui | eAWI_RESPONSE | eSTRING_ID | ui | ["..."] |
| Response option Position | Response option 1 | Response option 1 Text-ID | Response option 1 Text-ID | Response option 2 | Response option 2 Text-ID | Response option 2 Text-ID | Response option 3 | Response option 3 Text-ID | Response option 3 Text-ID | Display is modal |
| | | | | | | | | | | |
| AWI_OPT_POS_CENTER | AWI_RESPONSE_OK | S_AWI_BTN_OK | | | | | | | | |

Message parameters, part 3

Fig. 6e

| BO | BP | BQ | BR | BS | BT | BU | BV | BW | BX | BY | BZ | CA | CB | CC | CD | CE | CF | CG | CH | CI | CJ | CK |
|---|---|---|---|---|---|---|---|---|---|---|---|---|---|---|---|---|---|---|---|---|---|---|
| message text | | | | system reaction (S/R) | | | | | | | | | S/R class process status | | | | | | alarm reset | | | EOL |
| AWI text | Response option 1 | Response option 2 | Response option 3 | Text (English) | | | | | | | | | | | | | | | | | | |
| | | | | SR_ArtClampClosed | SR_VenClampClosed | SR_VenClampOpened | SR_BloodPumpStop | SR_Reaction 4 | SR_Reaction 5 | ... | ... | SR_Reaction Z | SZ_blood | SZ_heparin | ... | ... | SZ_PatDisconn | Self-deleting message | Self-deleting system reaction | Dead time after key "OK" | Dead time after key "ignore" | |
| | | | | [" "] | | | | | | | | | [" "] | | | | | | [" "] | ui [s] | ui [s] | EOL |
| Art. Pressure< user limit | OK | | | | 1 | | 1 | 1 | 1 | 1 | | | 1 | | | | | | | 1 | | EOL |

Fig. 6f

COMPUTER SYSTEM AND METHOD FOR CREATING AT LEAST ONE MACHINE-READABLE FILE FOR A MEDICAL TREATMENT APPARATUS

CROSS REFERENCE TO RELATED APPLICATIONS

This is a 371 national phase application of PCT/EP2010/002492 filed Apr. 22, 2010, claiming priority to German Patent Application No. 10 2009 018 806.1 filed Apr. 24, 2009.

FIELD OF INVENTION

The present invention relates to a computer system. It further relates to a data medium and a medical treatment apparatus. In addition, it relates to a method, a digital storage medium, a computer program product and a computer program.

BACKGROUND OF THE INVENTION

Medical treatment apparatuses like, for example, dialysis apparatuses are controlled or regulated by means of a firmware which is normally elaborate. This software often encompasses several thousand program lines which regularly are programmed in advanced programming languages such as $C^{++}$, which are not intuitively accessible. The source code on which such software is based usually gets more elaborate and often more complex with each software update and with each new software version. Modifications to the software such as are required, for example, for an update, therefore have to be entered by a highly qualified programmer. As creating software still is extremely individual work, modifications often have to be carried out even by the same programmer who has already programmed the preceding software versions, if additional effort and expenses for training another programmer for the already existing program design or style should be avoided. The effort in carrying out necessary modifications to the software is, however, extraordinarily high in any case. The same applies to the expenses associated therewith.

Modifications to the software due to changed requirements for the process of the medical treatment apparatus operated with the software require after each modification qualifying or approving not only the modified functions, but also all previous functions of the whole device for verifying its perfect functioning. This may, with more complex systems such as for example dialysis apparatuses, lead to an often immense number of cases to be tested and the associated effort.

As for changing the flow or process behavior by modifying the software, up to date programming skills are necessary; only software developers can modify the flow behavior of the firmware. Process developers who usually are not software specialists, however, often cannot carry out these modifications, even though they in turn know the medical treatment methods best and are especially well-trained for modifying or changing the flow behavior of the corresponding apparatuses. Also this fact leads to effort and expenses due to the required coordination between programmer and process developer. Furthermore, the error probability of the work increases due to communication difficulties.

SUMMARY OF THE INVENTION

The present invention is based on the object of proposing a computer system for simplified execution of software modifications or for reprogramming flow patterns of a medical treatment apparatus that are influenced by the firmware. Further, a data medium and a medical treatment apparatus are to be specified. In addition, a corresponding method is to be shown.

The computer system according to the invention (in short: system) encompasses at least one memory or one database for creating at least one machine-readable file for a medical treatment apparatus (in particular for a dialysis apparatus), in particular for operating, controlling or regulating it. The computer system according to the invention is in certain embodiments according to the invention intended and/or configured and/or used for the aforementioned creation.

The database may be an SQL database known to the person skilled in the art or any other suitable database.

In the memory or in the database, data which is relevant for operating a medical treatment apparatus may be saved transiently (only while memory or database is supplied with current or power) or permanently (also after disconnecting a current or power supply) and optionally serviced.

The saved data may preferably be or encompass parts of or the entirety of all data relevant for operating the medical treatment apparatus.

The saved data may preferably be used for parameterization of treatment-specific flows which are encoded in inherent program sections.

This data may be present in the form of one or several parameter sets or a source code of at least one first programming language. It may also be present in the form of a file which was generated from such a parameter set or source code of a first programming language or in the form of a program generated therefrom—in particular a non-machine-readable program.

The system which may be represented by means of a single computer or a combination of several devices—computers or other apparatuses—further comprises at least one input device.

The input device may encompass or be an interface software.

The input device may be designed for manual input of data such as a keyboard, a computer mouse, a stick or the like. However, it may also be designed in any other way that is familiar to the person skilled in the art for the purpose according to the invention.

The input device may have ready forms prepared for facilitating entries and for preventing erroneous entries in which the user may make entries without special programming skills, and is optionally led by the system, which reflect modifications or new routines in the process of the medical treatment apparatus.

The interface or the forms may be structured to be generally intelligible. They may be equipped with user assistance.

The entries may hereby be checked for logic and compatibility with other entries or known remaining data by the system. Irregularities recognized hereby may be communicated to the user.

Entries in the input device or the forms provided herefor thus do not require the assistance of a highly qualified software developer but they can be carried out, e.g., by the process developer him- or herself.

The database and the input device may be on a host or work station of the process developer. They are thus operable independently of the presence of the medical treatment apparatus.

The data to be entered by means of the input device which concern the flow behavior of the medical treatment apparatus may hereby be entered in a format which corresponds to the format of the at least one parameter set and/or a programming language which is not the first programming language and/or file formats originating herefrom or the like.

The input data may be saved and optionally serviced in the database.

The system further comprises at least one output device, e.g., in the form of a monitor, a printer or the like, for creating and outputting a flow (or process) definition output file. The output device according to the invention is in certain embodiments according to the invention provided and/or configured and/or used for the aforementioned creation and output.

The flow definition output file may be a text file in "*.csv" (character-separated values) format.

In the flow definition output file, all relevant flows and/or flows to be changed and/or processes or routines to be entered anew, preferably with all necessary details, comprehensible to the process developer, optionally accordingly prepared, may be listed.

Checking the data entered by means of the input device may therefore be carried out clearly and transparently with the flow definition output file for example for preventing or easier locating of input errors. It thus advantageously contributes to decreasing the error rate in programming.

The flow definition output file may hereby be presented on the monitor, however, it may also be output on paper. The latter may serve to improve legibility and thus advantageously decrease the risk of missing an error in the file or in the processes to be defined. Furthermore, any other suitable way of reproduction may be used.

The system further comprises at least one converting device—this may be a computer, a device hereof and/or a computer program—for creating at least one machine-readable file or machine-readable data present in a storage medium, based on the first program section and/or the parameter set and/or the flow definition output file or, respectively, the input data (i.e. the entered data) represented in it. The converting device is in certain embodiments according to the invention intended and/or configured and/or used for creating the aforementioned.

Another (interface) software may be used in the converting device.

By means of the converting device, the flow definition output file is converted to, e.g., so-called header files ("*.hpp").

The format of the files into which the conversion is to be made may preferably be processed in the utilized programming language by means of the compiler. For example, these may be "*.hpp" header files for $C^{++}$.

By means of the converting device, machine-readable files—in particular those that are meeting the demands and which are also called code files—or machine-readable data may be created. The machine-readable file or the machine-readable data in a storage medium (the two last mentioned terms are interchangeably used in the present invention) may hereby be understood as one single file or also as a group of connected or interacting files, furthermore as at least one file with at least one sub-file.

Converting may according to the invention in particular be understood as format converting of the flow definition file or the data contained therein into a machine-readable form. Preferably, no further information beyond the information of the database or the flow definition output file are or will be added, transformed or saved in this process. In particular, preferably no information relevant for the operation of the medical treatment apparatus is added, transformed or saved.

The system according to the invention may be executed on a computer of the process developer, as mentioned above. Its result (e.g., the generated header files) may be modified together with the operating program of the device and a corresponding flow tracing device using a compiler into a program code which for example is filed and executed in a memory of a medical treatment device.

For example, in a preferred embodiment, it is proposed that the output device is suited and prepared to output a flow definition output file with at least one spreadsheet having rows and columns.

Due to its structuring in columns, rows, cells and spreadsheet areas, such an output format is suitable for a particularly informative and clear representation of the flow definitions entered by means of the input device. This representation thus contributes to reducing the risk of missing an input error.

In a further preferred embodiment, the system according to the invention comprises an output device for outputting a spreadsheet of the flow definition output file which is subdivided in units. Hereby, the spreadsheet comprises at least information from a group which encompasses at least detection statuses, a distribution list, a process block, a system status block and a reaction block. This information may be accordingly prepared in rows and/or columns. Hereby, the reaction block may contain predefined information which leads, e.g., to an alarm-caused activation of the actuators of the medical treatment apparatus which is operated resulting in the system according to the invention (clamps, valves, pump drives, and so on).

The units may each cover a predetermined or a dynamically or otherwise variable number of columns and/or rows. Each cell may hereby have, e.g., either the entry 1 or 0, depending on whether a status applies (1), or not (0). This facilitates checking the entered values. It is possible according to the invention to execute the flow definition output file by using a commercial spreadsheet software program such as, e.g., Microsoft Excel™, in which cells of a worksheet are occupied by means of entries in rows-and-columns format in a known manner. Rows which hereby overlap all units may each depict one of the conceivable flow situations and flow reactions due to the combination possibilities of process options and system status.

In a particularly preferred embodiment, the flow definition output file may encompass an alarm definition spreadsheet (in short: ADT). The tabular form is an especially clear display format in which flows and coherences such as for example alarm statuses may be illustrated in a simple intuitive way.

The object according to the invention is also accomplished by means of a preferably digital data medium with at least one machine-readable file or machine-readable data in a storage medium created by means of the system according to the invention. The data medium may, as proposed in a further preferred embodiment, comprise a multitude of machine-readable files or machine-readable data created by means of the system according to the invention, wherein at least two files from the multitude of machine-readable files or sets of machine-readable data differ from one another. Providing different machine-readable files is in particular useful and advantageous when a medical treatment apparatus comprises a multitude of CPUs among which at least two CPUs require different information during operation of the medical treatment apparatus.

The data medium may hereby be a common memory or memory device. It may save temporarily, but it may also be a permanent memory. It may be a stationary memory or a mainly transportable data memory.

The object according to the invention is further accomplished by means of a medical treatment apparatus that may in particular be designed as dialysis apparatus, e.g., for performing an HD (hemodialysis), HDF (hemodiafiltration), a CVVH (Continuous Venous Venous Hemofiltration), CVVHD (Continuous Venous Venous Hemodialysis) CVVHDF (Continuous Venous Venous HemoDiaFiltration) or other therapy methods.

The medical treatment apparatus comprises in a preferred embodiment a ROM in which the machine-readable file created by means of the system according to the invention or a data medium comprising such files is filed or saved. In a further preferred embodiment, the medical treatment apparatus comprises a flow tracing device. In an again further preferred embodiment, the medical treatment apparatus comprises a ROM in which an alarm status tracing device or an alarm handler code is filed.

By means of the present invention (i.e. by means of the system, the data medium, the medical treatment apparatus and the process equally), it is advantageously possible to determine, save and, if required, to change flow definitions in a centralized way. The flow definitions which may be for example alarm definitions, i.e. definitions of alarm statuses, may by means of the present invention be "extracted" basically from the source code of the software used for operating the medical treatment apparatus. For this, a modular structure which is easy to service is proposed, in which all information required for illustrating the system behavior may be managed at one single location and illustrated in a form which can be entered and for example reliably read for control purposes also by a non-programmer, e.g., the process developer. Qualifying or approving the firmware is therefore reduced to the control of the entered details and structures and optionally to random tests of the device behavior after modifications to the firmware.

Another advantage of the system according to the invention is that after the initial qualification or approval of entered modifications or supplements, the effort for further modifications is significantly reduced as compared to the methods or systems known from the status of the art. There, the approval effort significantly increases with each further modification.

A further advantage of the system according to the invention and the method based on it is the transparent and easy programming. This leads to an effective reduction or even prevention of errors in processes or in the source code.

The approach proposed according to the invention thus advantageously allows managing all information required for illustrating the system behavior at a central location and representing it in a form which is also "readable" for someone who is not a software developer.

Thus, according to the invention, "reprogramming" or an update of the firmware or of parts hereof of a medical apparatus such as, e.g., a dialysis apparatus may reliably take place with little effort and nearly no programming skills.

The present invention is hereafter exemplarily explained in detail with the appended drawings. In the description of the figures, terms are used which hereafter are defined with validity only for the description of the figures. It applies that:

ACG stands for "Advanced Code Generator", an auxiliary program which converts the data of the ADT (in CSV format) into an internal format which subsequently can be read by the compiler or the converting device.

ADT stands for "Alarm Definition Spreadsheet". This is at least one file in CSV format in which all information required for the processing of the alarm is contained. The ADT is subdivided into the preprocessing spreadsheet, the detection spreadsheet and the relevance spreadsheet.

"Alarm handler" or alarm handler code stands for a part of the firmware; the alarm handler represents a part of the code which processes the information that is taken from the ADT (and transformed with the ACG) and initiates the reactions defined in the ADT.

"AWI" stands for a prefix which relates to the handling of the message (alarm, warning, info).

"AWI-ID" stands for a definite number for allocating and designating a message.

A treatment process is understood as a flow definition for a medical treatment, e.g., CVVHDF, SCUF, HD process and HDF process. In a firmware, the option to perform different treatment processes is usually implemented. The treatment process to be performed currently is determined by the user.

"Compiler" stands for a commercial program which creates a binary code (program code) from the source code (written in a programming language) which is processed by the respective microprocessor.

CPU is a synonym for the microprocessor; a device or an apparatus may contain several CPUs which share an overall task.

"CSV format" stands for "Character-Separated Values", a text-based exchange format which is common in the field of electronic data processing and which can be visualized in a structured way with, e.g., Microsoft Excel™.

The "Enable column" is part of the detection spreadsheet; in the Enable column, it is determined whether the condition definition starts in this row, or whether an AND-conjunction with a previous spreadsheet row exists.

In the "detection spreadsheet", values (of variables and/or constants) are linked with conditions or attributed thereto. The result of a conjunction is a "detection status".

A "detection status" stands for the result of a comparison or a Boolean operation. It represents a logical status (true or false) depending on whether the underlying condition is met or not.

The "firmware" encompasses all modules (data modules and program modules) which are implemented in the program code by the compiler. If or when several microprocessors are used in the device, the firmware encompasses all modules of all processors.

A "device status" is the status of one or more device components such as, e.g. "clamp 1 is open", "pressure A is larger than <value>".

"Internal format" means, using the example of the C/C++ compiler, the arrangement of data in header files (e.g., "*.H" or "*.HPP").

The "program code" (also binary code) is present in the memory of the device and is processed during operation of the device by the corresponding processors.

A "system status" signals that during a treatment process the device may be in different statuses such as "initial test", "device test", "set up", "prepare", "fill", "rinse", "treat", "error", "switch off", and so on.

"Sensor values" are variables which denote values of associated sensors. These are for example pressures, voltages, flow values, and so on.

"Sub-processes" are understood to be alternatives or optional additives or supplements during a treatment process. E.g., the anticoagulation of blood may be supported during each process by means of heparinization or the administration of citrate/calcium as an example for a sub-process.

The "system reaction" defines the behavior of the device in a certain device status. The system reaction is component-based (pumps, clamps and so on). The entirety of all system reactions basically is the system behavior.

The "system behavior" determines how the devices should handle values and statuses. The system behavior is realized by means of the programming (firmware).

"Process status" is a special status of the device which relates to several components; for example, the following can be defined:
SZ_blood blood system stopped
SZ_balance balancing stopped
SZ_FPSA FPSA stopped
SZ_CiCa CiCa stopped
SZ_heparin heparin stopped
SZ_PatDisconn patient disconnected.

The term "preprocessing spreadsheet" stands for a subarea of the ADT and defines whether and how individual sensor values and status values are preprocessed.

Preprocesses are for example arithmetic averages, detection algorithms and elimination algorithms for artifacts, and so on.

BRIEF DESCRIPTION OF THE DRAWINGS

In the drawings, same reference numerals refer to the same or identical structures. It applies that:

FIG. 4 reproduces a spreadsheet according to the invention with parameters for preprocessing.

FIGS. 5a and 5b reproduce a detection spreadsheet according to the invention.

FIGS. 6a to 6f reproduce a relevance spreadsheet according to the invention.

DETAILED DESCRIPTION OF THE DRAWINGS

Figure 1:
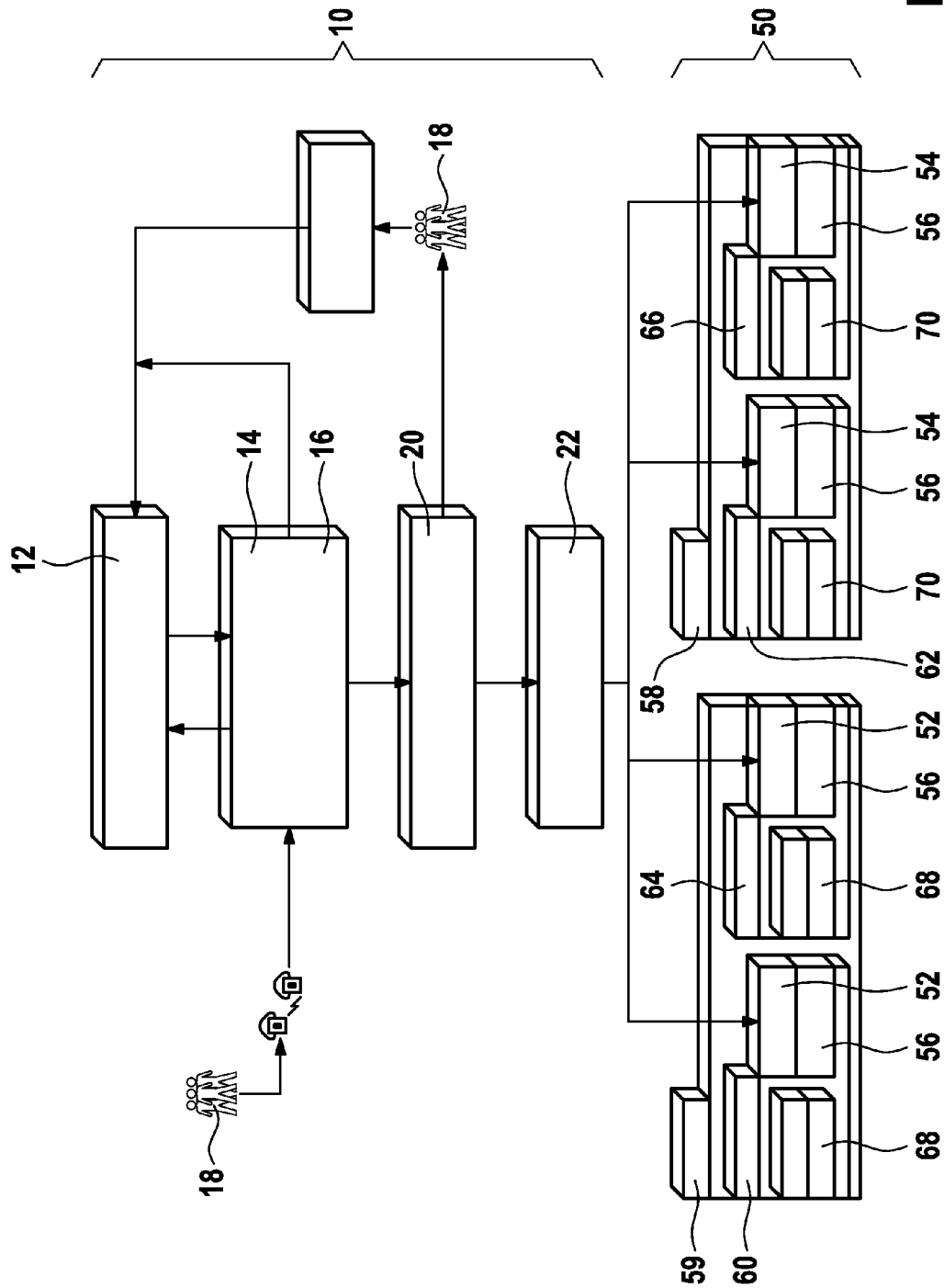
FIG. 1 shows a schematic construction of a system according to the invention in its interaction with a medical treatment apparatus according to the invention.

FIG. 1 shows a system 10 according to the present invention as well as sections of a medical treatment apparatus 50 which in the example of FIG. 1 is embodied as dialysis apparatus. Hereby, the system 10 is arranged outside and independent of the medical treatment apparatus 50. The system 10 which, e.g., is present on the external computer of a process developer, comprises i.a. an SQL database 12 for saving/storing and managing data which is relevant for the operation of the medical treatment apparatus 50.

Inputs and outputs of files into the system 10 and in particular into the database 12 take place via a separate tool, namely the input device 14, which in the example of FIG. 1 is at the same time used as output device 16. This tool may be denoted as Alarm Database Interface (ADI) in the case that the system serves to determine alarms, as indeed is the case hereafter. In the tool 14, 16, form sheets, which are utilized both by software developers and by process developers, are used for the entry. Entry by means of form sheets or templates advantageously allows that if modifications to the reaction of the devices is desired—e.g., in the case of an alarm in which the machine should not just indicate an alarm acoustically, but in addition also optically—, the software engineer no longer has to formulate a new source code, but the process developer 18 has to carry out the associated entries and thus define or specify a new alarm behavior of the machine at a separate workplace via an entry form of the input device 14.

If all detection statuses or all data required for the modification are entered, the output device or the ADI tool 16 generates a flow definition output file which in the example of FIG. 1 is a text file (*.csv) in the form of a spreadsheet, the so-called "Alarm Definition Spreadsheet" or ADT 20. In this flow definition output file or ADT 20, all relevant or even conceivable alarm situations and alarm reactions are listed in tabular form. In this form, the entered data is easy for the above-mentioned developer or a different development team 18 to check. This may be carried out, e.g., by means of paper review. Should changes in the flow definition output file 20 be required, they will again be filed in the SQL database 12 via an entry form of the input device 14, simplified, and output as text file in tabular form.

Hereby, any number of review steps may be carried out. However, as in any case only the changes as compared to the previous version have to be checked, additional flow definitions or alarm definitions and instructions for a correspondingly changed alarm behavior may be added without much effort.

If or when the flow behavior or alarm behavior is finally described or filed in the text file and approved or checked, the flow definition output file or ADT 20 is converted by a converting device 22 which in the example of FIG. 1 is embodied as a so-called Alarm Code Generator (in short: ACG) into a machine-readable file or data 52, 54 which is present in a storage medium, which in FIG. 1 is embodied as a so-called header file (*.hpp).

In the section of the medical treatment apparatus 50 illustrated in FIG. 1, a flow tracing device in the form of an alarm handler code 56 is provided by means of which the machine-readable files 52, 54—which may in general terms also be saved machine-readable data—are readable.

By means of the converting device 22, the different CPUs of the medical treatment apparatus may be taken into account. I.e., a machine-readable code of identical structure is always generated, however, it is individually adapted to the different functions and requirements of the various CPUs of the medical treatment apparatus 50. For example, the operation CPU of the monitor 58 does not have to receive exactly the information which the protection CPU 64 of the process control receives, e.g., for closing a venous clamp. The converted or compiled codes which are present in the machine-readable files 52, 54 may during the production of the medical treatment apparatus 50 be burned in the ROM memory of the delivered treatment apparatus 50 for example, and are thus unchangeable. The machine-readable files 52, 54 may however also be integrated in the treatment apparatus 50 as part of an update at a later time after delivery of the medical treatment apparatus 50 to the user. The instructions for processing the flow definition are on each CPU identical in the alarm handler code 56.

Thus, all data used for the flow of the process are saved in the ROM of the treatment apparatus 50. The machine-readable contents of the flow definition output file 20 as well as an instruction how these data are to be treated are also present in the ROM. These fixed data are supplemented by dynamically generated, changeable data from flows and monitorings, such as regulating values, sensor values, ambient parameters and the like. These changeable values act upon the flow tracing device 56.

Besides the above-named and further components which are not further discussed here, the treatment apparatus 50 of FIG. 1 comprises i.a. a first operation system 60 for a treatment section 59 of the treatment apparatus 50 on which the method for the treatment takes place, and a second operation system 62 for the monitor 58. It further comprises a first protection system 64 for the treatment section 59 of the treatment apparatus 50 and a second protection system 66 for the monitor 58. A first device 68 for saving or storing process flows or operation flows of the treatment apparatus 50 and a second suchlike device 70 for the monitor 58 are each present twofold. The treatment apparatus 50 is doubled in its essential components for security reasons. In the example of FIG. 1, it comprises four CPUs among which two are provided for operating the medical treatment process (one CPU for the operation system and another one for the protection system) and separately two other CPUs are provided for the display area (monitor 58) which does not have any retroactive effect on the treatment process.

The example of FIG. 1 is aimed at determining alarm statuses. The present invention is, however, not limited to this, but may be aimed at any flow and process of the medical treatment apparatus.

Figure 2:
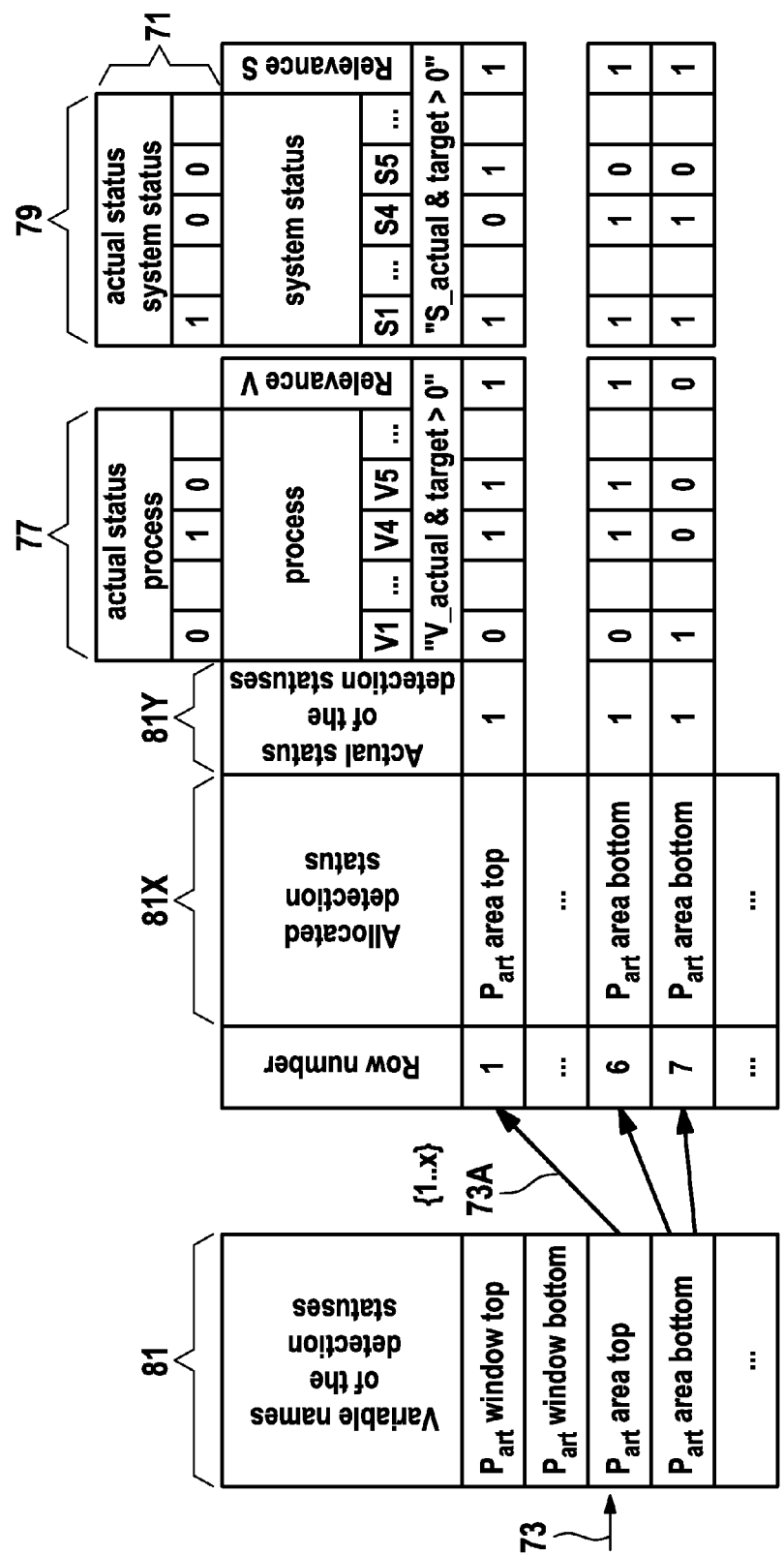
FIG. 2 shows an example of an assessment of relevance according to the invention, in order to initiate a correspondingly predefined reaction of the medical treatment apparatus when or if the result is positive.

FIG. 2 shows, with the example of a permanent sensor, monitoring an assessment of relevance in order to initiate a correspondingly predefined reaction of the medical treatment apparatus if the result is positive. If or when an upper limit of the value measured by the sensors is reached (e.g., the upper limit of the arterial pressure window), this does not yet require an alarm, but only represents a detection status. Now, it is decided whether this detected status is of relevance and thus an alarm is to be given. The flow tracing device 56 (which in the example of FIG. 2 is an alarm status tracing device or an alarm handler code and is hereafter also referred to as such alarm status) permanently reads row per row the content of the alarm definition spreadsheet illustrated in FIG. 2 and receives in the column "allocated detection status" 81X the reference to a defined detection status 81 which for example as referred to with 73 or 73A represents a transgression of the upper limit area for the arterial pressure. The actual statuses 81Y (current device statuses) of the allocated detection statuses define the relevance of the rows. A "1" means that the row has to be edited. In simplified terms, the row-by-row processing runs through three blocks, namely the process block 77, a system status block 79 and a reaction block which is not shown in FIG. 2.

In the illustration shown in FIG. 2, all detection statuses are represented in a first block which is in FIG. 2 depicted in a simplified way by means of a first column 81. Thus, in the first column of each row of FIG. 2, a detection status is reproduced each one of which is in generally intelligible plain text referred to as, e.g., "blood pump standstill", "transgression of the limit window of the arterial pressure", "blood pump does not rotate" or "transgression of the limit area of the arterial pressure" and so on.

Defined detection statuses 81 may be listed in several rows 73A in the column "assigned detection status" 81X and be relevant for arbitrary processes and for arbitrary system statuses.

The process block 77 encompasses several columns and indicates all conceivable processes or sub-processes of the medical treatment device in columns V1, . . . , Vx. Thus, one column of the process block 77 is allocated to each known or possible medical treatment method. In its cells, an entry of "1" or "0" is made, depending on whether the detection status is relevant for the respective process of a column ("1") or not ("0"). If or when the alarm handler code has entered a row, it detects for the process V1 which for example stands for "Single Needle Process" or "HD Process", a "0" and in the process V4 and V5 each a "1". Thus, the detection status would be relevant in two processes. However, the alarm handler code needs the information in which process or treatment the medical treatment apparatus currently is. The alarm handler code receives this information via dynamic data from the flow or process monitoring. These reproduce the current status of the treatment apparatus. The results are listed as "0" or "1" in the spreadsheet of FIG. 2 in the top row, row 71. Thus, in the example of FIG. 2, there is consistency in V4 and no consistency in V5. However, as already one single consistency is relevant, the alarm handler code will further run through the row to the right.

The alarm handler code or alarm handler now gets to the system status block 79. There, all possible system statuses or all possible or relevant temporal phases of the medical treatment processes such as "filling", "treatment", "downgrading" and so on are recorded in columns. Just as previously in the process block 77, the statuses or their combination possibilities are marked with "0" and "1". In the example of FIG. 2, system statuses S1 and S5 could therefore be relevant, wherein considering the dynamic data of the current system status there is only a concordance and thus a relevant status with S1. The result of the assessment of relevance of the process block 77 and the system status block 79 is each a "1". Thus, an overall or general relevance is given. Systematically, the spreadsheet would now have the identical structure to the right, wherein then all further system reactions would be listed there. This is not shown in FIG. 2 just for the simplification of the illustration.

If during the row-by-row processing it is determined at one point in a row that there is no relevance, the rest of this row is skipped and the next row of the spreadsheet or the distribution list is processed in the same way.

The task of the alarm handler code, which may be filed as software in the ROM of the medical treatment apparatus, is thus limited to a very simple, standardized processing of Boolean operators of the alarm definition spreadsheet. Because of this, the alarm handler code is advantageously easy to check for correctness or to approve and also usable in the same way at many other places.

According to the present invention, it is readily possible to define additional statuses or reactions of the medical treatment apparatus when using the tabular form for the flow definition output file. This requires only the inclusion of a further column and/or row in the respective units. Such an inclusion may take place by the input device in an automated way.

The spreadsheet for the flow definition output file may further also comprise cells, which during operation of the associated medical treatment apparatus, are dynamically covered based on the flow monitoring and which reproduce the actual status of the medical treatment apparatus during their operation.

The combination of all information in one definition spreadsheet (ADT=Alarm Definition Spreadsheet) has i.a. the following advantages:

All information relevant for the system behavior is centralized;

The information is present in a form which is also readable for people that are not software developers (no special know-how in a certain programming language required);

For realization of the system behavior, only a part of a code is generated for the firmware (also called alarm handler) which runs through and evaluates the information and initiates the associated reactions;

Converting the spreadsheet information into a form the alarm handler can process is carried out with a conversion program or a converting device (ACG=Advanced Code Generator); by means of the automated implementation, errors are minimized;

Changes in the specification of the system behavior exclusively take place through modification of the spreadsheet information (possible exception: new "features" are integrated in the spreadsheet; then, also a modification of the alarm handler is required);

Add-ons or modifications may be carried out in a simple way without impairing the flow of the other firmware; and The spreadsheet at the same time represents a documentation; it is not necessary any more to generate or service the latter separately.

Figure 3:
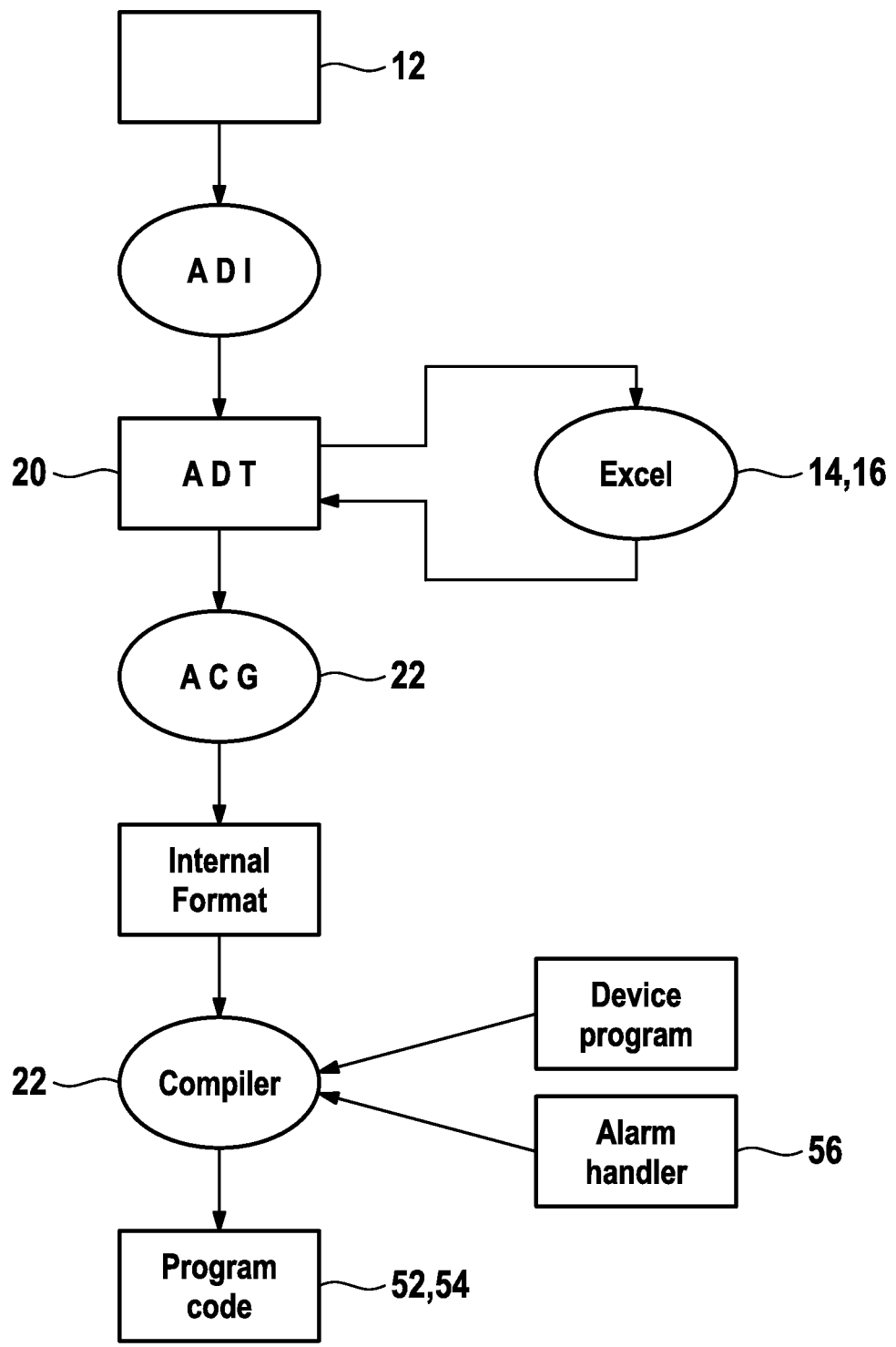
FIG. 3 shows in the form of a flow chart data structures and program structures according to the invention in its processing.

FIG. 3 shows in the form of a flow chart data structured and program structures in their process flow with the example of determining alarm statuses in a method according to the invention. Rectangular areas in FIG. 3 stand for data objects, oval areas for programs and program parts. The alarm definition spreadsheet ADT 20 (in CSV format) is processed for example with Microsoft Excel™ (or a comparable spreadsheet calculation program) or a simple text editor or the like as input as well as output device (reference numeral 14 respectively 16). With the tool ACG, it is afterwards converted to a form "internal format" which is usable for the utilized compiler or conversion code. The latter generates the actual, machine-readable program code from the data of the data of the ADT 20 together with the code part for the alarm handler 56 and the remaining device program.

The information of the flow definition output file is saved in three tables "preprocessing", "detection", "relevance".

During preprocessing, such as is illustrated in FIG. 4, it is determined whether and possibly which "raw measurement values" run through which mathematical transformation such as averaging, scaling, filtering or the like. As further filtering ways, for example averages, calculations of polynomials and so on are conceivable.

In the first column block ("CPU"), these microprocessors are marked on which the preprocessing should take place. In the second column block ("preprocessing parameter(s)"), it is determined which raw data (variable) of which type is mathematically transformed in which way. In the above example, a raw pressure "Pressure_PS_01_CalcValue" (sensor value of a pressure sensor PS1) is sent through a mean filter of the dimension 6. As output value, a variable "Pressure_PS_01_CalcValue_AVGA_6" is defined which contains information on the utilized filter already in its name. The output variable is automatically generated by the tool chain by providing a formula, however, it may also be overwritten manually. Automatic generation has the advantage that double entries generate identical variable names and lead to an error message during the final converting process or compiling process at the latest.

In the spreadsheet "detection", as shown in FIGS. 5a and 5b, values are linked to conditions with the aim of receiving a logical value (yes/no; true/false) as result. These resulting logical values are called detection statuses. They describe the current status of a device or a component, for example "clamp A is open" or "pressure B is higher than a limit value".

The detection spreadsheet (as also the preprocessing spreadsheet) is completely cycled, i.e., after each run, current values are available in the detection statuses.

Per row, a comparative operation may take place. Typical operations are "EQ" (equal), "LT" (less than), "GT" (greater than), but also "DGT" (difference greater than). More complex conditions are realized, e.g., by connecting several spreadsheet rows in series. This results in a logical "AND"-conjunction. "OR"-conjunctions are realized by separate spreadsheet rows.

This shall at first be explained in general. A concrete example is explained farther below.

In the spreadsheet of FIG. 5a, each row again begins with the indication of the target CPU.

After that, the enable column follows which is used for the AND-conjunction. If here there is a "1" in a row, this is a row in which a condition definition starts.

Subsequently, the specification of the condition takes place, consisting of a variable name, a comparative operation and a second value. This second value may either be a variable again or a constant (literal).

The result of the formulated condition is then filed in the specified detection status (realized as variable). The identification of the detection status variable, just as during preprocessing, takes place automatically and hereby generates clear specifications.

In a concrete example, this may turn out as follows, wherein the example is an extract of a pressure monitoring. In the second row, the value of the variable "T0_Part_UserLowerThresholdInactive_Counter" (serves to deactivate the pressure window for a certain time) is checked for equality with 0. The result is filed in the detection status "T0_Part_UserLowerThresholdInactive_Counter_EQ0".

The detection status will take on the value "yes" when the time meter for deactivating the arterial pressure has counted down to 0. In row 8 of the above example, this detection status is used as Enable, i.e. for generating an AND-conjunction. In the second part of the AND-conjunction, the averaged pressure known from preprocessing "Pressure_PS_01_CalcValue_AVGA_6" is checked as to whether it is less than (LT) the value of the variable "CPU1_USER_Pressure_Art_LowerWindowLimit" (i.e., the value set by the user). The logical result of the overall condition is then filed in the detection status "T0_Part_UserLowerThresholdInactive_Counter_EQ0_Pressure_PS_01_CalcValue_AVGA_6_LT_CPU1_USER_Pressure_Art_LowerWindowLimit".

This way, the condition formulated in prose "once the dead time has run out and the arterial pressure is below the lower limit set by the user" is represented in the detection spreadsheet. Obviously, there are no special programming skills required for this.

The same way, the condition put up in rows 13 and 14 may be interpreted as "in case the pressure block 1 should be started up, however, the available pressure is greater than 120 [mmHg], then . . . " <this has to be prevented as otherwise the tube system is damaged>. This consequence, which was added here as information, is not part of the detection spreadsheet, but reproduced in the following relevance spreadsheet of FIGS. 6a to 6f.

In the two steps so far, the raw data is preprocessed and device statuses detected by means of (complex) conditions. In this step "relevance" (see FIGS. 6a to 6f), the evaluation of these statuses and the formulation of the respective "then"-action takes place.

According to the underlying concept, the alarm handler checks the content of the relevance spreadsheet row per row during runtime of the firmware. Hereby, the check is only carried out as far as the defined conditions are valid. If, for example, the treatment process HD process is active, but the processed row in the column HD process is not marked, processing of the row is disrupted at this point and continued with the next row.

If or when all conditions in a row are processed completely (and positively), the alarm handler subsequently gets to entries that lead to a system reaction. Here, it is determined which actions have to be carried out due to the defined conditions.

The structure of the relevance spreadsheet of FIGS. 6a to 6f is hereafter explained with an example.

In FIG. 6a, again the CPU at which the system reaction is to be initiated is initially determined. Afterwards, the detection status is defined which is taken from the detection spreadsheet of FIG. 5.

In the next three column units of FIG. 6b, it is defined whether this detection status has to be considered (i.e. is relevant) for the current treatment process, for the current sub-process or in the current system status.

The exemplary processes named there range from "HD process" through "HDF process" to "process X"; the actual scope of the process is, however, changeable according to the invention and may encompass processes such as "Coraffin", "SCUF" and the like. If in a column a "1" is entered, and if the currently chosen treatment process matches the one named in this column, the detection status defined in this row is further regarded by the alarm handler. If the respective cell is not marked, the alarm handler may disrupt the evaluation of this row as it is not relevant for the current process.

For the sub-process (for example anticoagulation heparin, CiCa and FPSA), an extended definition applies: if a "1" is entered in the respective column, this row is relevant for the active sub-process. However, if an "x" is entered, this row is relevant independent of whether the respective sub-process is active or not. No entry (or "0") means that this row is not relevant for the given sub-process.

The evaluation of the program status (also called system status) takes place analogously. In the spreadsheet of FIG. 6b, a column exists for each defined program status. These are representatively the columns "device start" to "shut-off". For the spreadsheet-based alarm handling according to the present invention, again neither the meaning nor the number of program statuses is important. However, it is important that there is a distinction as to which system status the medical treatment apparatus currently is. A "1" in the respective rows/columns-combination means that the defined row is relevant when or if the current program status matches the one named in the column.

This again shows one of the advantages of a spreadsheet-supported definition. If monitoring (defined in the detection spreadsheet and resulting in a detection status) should be activated, e.g., for another method, a simple entry in the matrix suffices. The same applies to the program status (e.g., when the pressure detection should be active not only in "treatment", but also in "rinse"). Also an absence of reaction regarding other program parts of the firmware may be ensured, as only additional "activations" take place, the existing ones are, however, not changed hereby.

The next two column units of FIG. 6b represent an exception. In the column "not relevant for process status", it may be defined whether a reaction should remain undone. If the system is already in a defined, secure status (such as, e.g., SZ_blood), for example a pressure problem may remain disregarded as the secure status is already achieved. These columns may serve to prevent multiple system reactions and misinterpretable subsequent messages. In the following column block "not relevant after process status for time", it is determined that, e.g., after a process status "SZ_blood" certain detection statuses should not be regarded for a certain time, for example because the system has to stabilize at first in this time span. Basically, these columns are thus used for making monitoring during this restart of a stopped process temporarily a bit "more tolerant".

The last block in FIG. 6b encompasses the "AWI parameter"; the "priority" designates the importance of a message linked to this row. The system reactions linked to this row are not prioritized and are executed in any case.

Furthermore, the rows of the relevance spreadsheet may be subdivided into groups. Thus, all further spreadsheet rows that are active and allocated to the same group and have the same or a lower priority may automatically be confirmed at the same time via messages that are confirmed by the user. In general, this information is also used for handling subsequent alarms.

The last column allows change of system status defines whether the device is allowed to change the system status with a row detected to be relevant. At some points, blocking this device behavior is useful. This may be the case, e.g., when in a spreadsheet row a detection status is defined according to which the filter is not completely filled. The apparatus cannot end filling as long as this condition is given.

The columns in FIGS. 6c, 6d and 6e represent a detailed specification of the display reaction or the interface to the user. Included are message texts, colors and formats on the screen, light signals, acoustic reaction, nurse call, and so on.

In FIGS. 6d and 6e, message illustrations for the screen are described. Hereby, it applies that:

AWI text ID is a definite number which defines the message text; the actual text is taken from the list with this number;

AWI text index may be a duplicate of the AWI text ID;

Embedded Alarm Object in the message window, an additional object is illustrated besides the text; example: when a pressure alarm is issued, an attention symbol which should additionally emphasize the importance of the alarm is embedded in the message window;

Text parameter 1-5 message texts may contain formattings for embedding current values into the message text; example: "pressure exceeds <p1> mmHg". At this point, the value of the text parameter 1 is displayed. Currently, there are a maximum of 5 parameters available. The names of the variables are entered;

Help text ID is an explicit number which defines the help text; the actual text is taken from a list with this number; may also be not defined, in this case there is no help with this message;

Auxiliary picture in the help window, a graph or diagram which is specified here may optionally be illustrated beside the text;

Frame color the message window is drawn with the specified color. The options are grey, yellow, red. Add-ons of further colors and/or frame properties are possible according to the invention;

Acoustic signal determines which audio signal is generated when this message appears;

Optical signal determines which color/color combination the light should show when this message appears;

Nurse call determines whether the nurse call has to be activated when this message appears;

Response option-position determines in which order the confirmation keys appear in the message window; here, there are options like centered, left-aligned, right-aligned, distances, and so on;

Response option 1 signal which is triggered when the first confirmation key is pressed in the device;

Response option 1 text-ID label of the first confirmation key;

Response option 2 see above

Response option 2 text-ID see above

Response option 3 see above

Response option 3 text-ID see above

Display is modal display option; the display may be overlapped by other objects on the screen;

The next column block of FIG. 6f with the heading message text initially starts with four columns which are used only for development purposes by the applicant and contain in practice the 'mini-copy' of the message definition. The next column block contains the system reaction. The following component-based system reactions are exemplarily defined:
SR_ArtClampClosed closing the arterial clamp;
SR_VenClampClosed closing the venous clamp;
SR_VenClampOpened opening the venous clamp (e.g., for pressure release);
SR_BloodPumpStop stopping the blood pump.

Further component-based system reactions such as the following ones as well as again further ones may, of course, also be defined:
SR_ArtClampClosed closing the arterial clamp;
SR_VenClampClosed closing the venous clamp;
SR_VenClampOpened opening the venous clamp (e.g., for pressure release);
SR_BloodPumpStop stopping the blood pump.

Further component-based system reactions such as the following ones as well as again further ones may, of course, also be defined:
SR_DialysatePumpStop stopping the dialysate pump;
SR_SubstituatePumpStop stopping the substituate pump;
SR_FiltratePumpStop stopping the filtrate pump;
SR_FPSAClampClosed closing the FPSA clamp;
SR_FPSAClampOpened opening the FPSA clamp;
SR_FPSAPumpStop stopping the FPSA pump;
SR_HeatingOff switching off the heater(s);
SR_CiPumpStop stopping the citrate pump;
SR_CaPumpStop stopping the calcium pump;
SR_HepPumpStop stopping the heparin pump;
SR__24V_Off switching off the 24V power supply (emergency switch-off);
SR_PowerOfftotal switch-off (a further emergency switch-off); and
SR_PGM_Error transition into the error status; no continuation of the treatment possible.

For carrying out the alarm handling, it is hereby not relevant which special system reactions are defined. This takes place depending on the device's component equipment or the type of treatment method. It is rather important that all actuators that may influence the treatment method in any way are listed and taken into account with the system reaction.

In the above discussion of FIG. 6b, the exception regarding the process status was already pointed out. In the next column block 'SIR class', exactly this process status is defined, i.e. the process status is put to the component-based, single system reactions which is then used for the further assessment of relevance. The last column block contains options which may lead to the deletion of the generated message.

With a self-deleting message, the message is deleted when the detection status changes to "false". With a self-deleting system reaction, the initiated system reaction is reversed when the detection status changes to "false". By means of the dead time after "OK", it may be specified for how long the detection status will not be taken into account when the message is confirmed with "OK". Via the dead time after "ignore", it may be specified for how long the detection status will be deactivated when the message is confirmed with "ignore".

The invention claimed is:

1. A computer system for creating at least one machine-readable file or machine-readable data which is stored in a storage medium for a medical treatment apparatus, said computer system comprising:
a database configured to provide at least one parameter set;
an input device configured to input data regarding the flow behavior of the medical treatment apparatus as a parameter set;
an output device configured to create and output a flow definition output file taking into account the input data; and
a converting device configured to create at least one machine-readable file or machine-readable data in a storage medium utilizing the flow definition output file,
wherein the at least one machine-readable file or machine readable data is configured such that it is machine-readable by a CPU of the medical treatment apparatus for operating, controlling, and/or regulating the medical treatment apparatus, and
wherein the output device is configured to output the flow definition output file in a format which contains server rows, columns, or both.

2. The computer system according to claim 1, wherein the operating, controlling, and/or regulating of the medical treatment apparatus comprises the use of a sensor.

3. The computer system according to claim 1, wherein the output device is configured to output the flow definition output file as at least one spreadsheet with several rows, columns, or both.

4. The computer system according to claim 3, wherein the spreadsheet of the flow definition output file is subdivided into units which comprise rows or columns for at least information chosen from the group consisting of: detection statuses, a distribution list, a process block, a system status block and a reaction block.

5. The computer system according to claim 1, wherein the flow definition output file includes an alarm definition spreadsheet.

6. The computer system according to claim 1, wherein the at least one parameter set is a treatment-specific parameter set.

7. The computer system according to claim 6, wherein the at least one parameter set is a treatment-specific parameter set for dialysis.

8. The computer system according to claim 1, wherein the at least one machine-readable file comprises a plurality of machine-readable files, or the machine readable data comprises sets of machine-readable data, wherein at least two files of the plurality of machine-readable files or two sets of the machine-readable data differ from each other.

9. A medical treatment system comprising:
a machine-readable storage medium comprising at least one machine-readable file or machine-readable that was created by a computer system, said computer system comprising:
a database configured to provide at least one parameter set;
an input device configured to input data regarding the flow behavior of the medical treatment apparatus as a parameter set;
an output device configured to create and output a flow definition output file taking into account the input data; and
a converting device configured to create at least one machine-readable file or machine-readable data in a storage medium utilizing the flow definition output file,
wherein the at least one machine-readable file or machine readable data is configured such that it is machine-readable by a CPU of the medical treatment apparatus for operating, controlling, and/or regulating the medical treatment apparatus, and wherein the output device is configured to output the flow definition output file in a format which contains server rows, columns, or both.

10. The medical treatment system according to claim 9, wherein the storage medium is a ROM, in which the at least one machine-readable file or machine readable data is filed.

11. The medical treatment system according to claim 10, wherein an alarm status tracing device is filed in the ROM.

12. The medical treatment system according to claim 11, further comprising a flow tracing device.

13. The medical treatment system according to claim 9, wherein the medical treatment system is configured to perform dialysis.

14. A method for creating at least one machine-readable file or machine-readable data present stored in a storage medium for a medical treatment apparatus by a computer system, comprising the steps of:
provisioning at least one parameter set in the computer system;
inputting data regarding the flow behavior of the medical treatment apparatus as a parameter set by an input device;
outputting a flow definition output file taking into account the input data by an output device; and
creating the at least one machine-readable file or machine-readable data present in a storage medium by using the flow definition output file,
wherein the at least one machine-readable file or machine readable data is configured such that it is machine-readable by a CPU of the medical treatment apparatus for operating, controlling, and/or regulating the medical treatment apparatus, and
wherein the output device is configured to output the flow definition output file in a format which contains several rows, columns, or both.

15. The method according to claim 14, wherein the flow definition output file comprises at least one spreadsheet with several rows, several columns, or both.

16. The method according to claim 15, further comprising:
creating the spreadsheet of the flow definition output file such that it comprises units which comprise at least rows or columns for information selected from the group consisting of: detection statuses, a distribution list, a process block, a system status block and a reaction block.

17. The method according to claim 14 in which the flow definition output file is created as an alarm definition spreadsheet.

18. The method according to claim 17, wherein the alarm definition spreadsheet comprises a preprocessing spreadsheet, a detection spreadsheet and a relevance spreadsheet.

19. The method according to claim 14, wherein the at least one parameter set is a treatment-specific parameter set.

20. A non-transitory computer-readable storage medium containing a set of instructions that causes a computer to perform a process for creating at least one machine-readable file or machine-readable data for a medical treatment apparatus, said process comprising:
providing at least one parameter set in the computer;
inputting data regarding the flow behavior of the medical treatment apparatus as a parameter set by an input device;
outputting a flow definition output file taking into account the input data by an output device; and
creating the at least one machine-readable file or machine-readable data present in a storage medium by using the flow definition output file,
wherein the at least one machine-readable file or machine readable data is configured such that it is machine-readable by a CPU of the medical treatment apparatus for operating, controlling, and/or regulating the medical treatment apparatus, and
wherein the output device is configured to output the flow definition output file in a format which contains several rows, columns, or both.

* * * * *

UNITED STATES PATENT AND TRADEMARK OFFICE
CERTIFICATE OF CORRECTION

| | |
|---|---|
| PATENT NO. | : 8,560,510 B2 |
| APPLICATION NO. | : 13/265388 |
| DATED | : October 15, 2013 |
| INVENTOR(S) | : Arnd Bruegferhoff et al. |

Page 1 of 1

It is certified that error appears in the above-identified patent and that said Letters Patent is hereby corrected as shown below:

In the Specification:

At column 15, line number 47,

Delete "block 'SIR class'," and replace therefor with --block 'S/R class'--.

In the Claims:

At column 16, claim number 1, line number 18:

Delete the word "server" and replace therefor with --several--.

At column 17, claim number 9, line number 2:

Delete the word "server" and replace therefor with --several--.

Signed and Sealed this
Third Day of June, 2014

Michelle K. Lee
*Deputy Director of the United States Patent and Trademark Office*